United States Patent [19]

Buising et al.

[11] Patent Number: 5,324,646

[45] Date of Patent: Jun. 28, 1994

[54] **METHODS OF REGENERATION OF *MEDICAGO SATIVA* AND EXPRESSING FOREIGN DNA IN SAME**

[75] Inventors: Charisse M. Buising, Des Moines; Dwight Tomes, Cumming, both of Iowa; Janice Schmidt, Saskatoon, Canada

[73] Assignee: Pioneer Hi-Bred International, Inc., Des Moines, Iowa

[21] Appl. No.: 817,205

[22] Filed: Jan. 6, 1992

[51] Int. Cl.$^5$ .......................... C12N 15/00; A01H 1/04
[52] U.S. Cl. .................... 435/172.3; 800/205; 800/DIG. 24
[58] Field of Search .................... 800/205; 435/240.4, 435/240.48, 240.49, 240.5, 172.3, 172.1

[56] References Cited

U.S. PATENT DOCUMENTS 5,015,580  5/1991  Christou ........................ 435/172.3

OTHER PUBLICATIONS

Brown, Daniel, "Germplasm Determination of in Vitro Somatic Embryogenesis in Alfalfa", *HortScience*, 23: 526-531 (Jun. 1988).
Chibbar, et al., "Microprojectile Mediated Delivery of Marker Genes . . . ", Abstract, *J. Cell. Biochem.*, (Suppl. 14E, 277) (1990).
Lonsdale, D., et al., "Transient Expression of Exogenous DNA . . . ", *J. Exp. Bot.*, (41:230, 1161-1165) (1990).
Tomes, et al., "Transgenic Tobacco Plants & Their Progeny Derived By Microprojectile Bombardment of Tobacco Leaves", *Plant Mole. Bio.*, 14:261-268 (1990).
Matheson, et al., "Selection of Regenerative Genotypes From Highly Productive Cultivars of Alfalfa", *Euphytica*, 45:105-112 (1990).
Busbice, T. H., et al., "Genetics & Breeding Procedures", *Alfalfa Science & Technology*, (Hanson, C. H., Ed.) pp. 283-318 (1972).
Review, "Alfalfa Germplasm in the United States", U.S. Dept. Agriculture Technical Bulletin No. 1571 (Nov. 1977).
Chabaud, Mireille, et al., "Parameters Affecting the Frequency of Kanamycin Resistant Alfalfa Obtained by Agrobacterium Tumefaciens Mediated Transformation", *Plant Cell Reports*, 7:512-516 (1988).
Delzer, B. W., et al., "Agrobacterium Tumefaciens Susceptibility and Plant Regeneration of 10 Soybean Genotypes in Maturity Groups 00 to II", *Crop Science*, 30:320-322 (1990).
Byrne, Michael C., et al., "Strain and Cultivar Specificity in the Agrobacterium-Soybean Interaction", *Plant Cell Tissue and Organ Culture*, 8:3-15 (1987).
Maheswaran, G., et al., "Direct Somatic Embryoid Formation on Immature Embryos of Trifolium repens. T. pratense and Medicago sativa, and Rapid Clonal Propagation of T. repens", *Annals of Botany*, 54:201-211 (1984).
Buising, Charisse, "Direct Introduction of DNA Into Embryonic Aces of *Glycine mas* By Microprojectile Bombardment", Dissertation Presented Apr. 17, 1992.
Deak, M., et al. Plant Cell Reports, vol. 5 (1986) pp. 97-100.
Brown, C., et al. Plant Cell Tissue Organ Culture, vol. 4 (1985) pp. 111-122.
Hazra, S., et al. Bio/Technolgy, vol. 7 (1989) pp. 949-951.

*Primary Examiner*—David T. Fox
*Assistant Examiner*—Charles Rories
*Attorney, Agent, or Firm*—Patricia A. Sweeney

[57] ABSTRACT

The invention relates to improved transformation and regeneration of alfalfa, *Medicago sativa*.

A method is used to transform alfalfa by using particle acceleration. Optimum results with mature cotyledons occurs when bombarding after 24 to 120 hours of imbibing water. Regeneration and transformation of alfalfa is greatly improved by using immature cotyledons or embryos of immature cotyledons for transformation and regeneration. Immature cotyledons include those up to about 25 days past pollination, and preferably include cotyledons excised at 10-15 days past pollination, most preferably including those excised at about 10 days past pollination. These cotyledons have a light green to translucent appearance. Plants resulting from bombardment of somatic embryos of immature cotyledons retain regeneration ability.

8 Claims, 5 Drawing Sheets ical transformation of plants has been one of the major advances achieved in biotechnology and its contributions to producing improved plants, improved crops, and consequently improved availability of food worldwide has been widely recognized. In certain plants, however, transformation has been especially difficult to achieve, and transformation of the valuable forage crop alfalfa, *Medicago sativa* has been inhibited by the peculiarities of the plant.

METHODS OF REGENERATION OF *MEDICAGO SATIVA* AND EXPRESSING FOREIGN DNA IN SAME

BACKGROUND OF THE INVENTION

Genetic transformation of plants has been one of the major advances achieved in biotechnology and its contributions to producing improved plants, improved crops, and consequently improved availability of food worldwide has been widely recognized. In certain plants, however, transformation has been especially difficult to achieve, and transformation of the valuable forage crop alfalfa, *Medicago sativa* has been inhibited by the peculiarities of the plant.

Transformation of alfalfa has been hampered primarily by two major limitations: constraints imposed by the method of transformation, and the poor regeneration from tissue and cell cultures of many alfalfa varieties.

The first limitation occurs because alfalfa is presently primarily transformed through the use of *Agrobacterium tumifaciens*. *Agrobacterium* exhibits host strain specificity and only certain *Agrobacterium* strains will infect a few alfalfa genotypes. The ability to transform alfalfa is considerably limited as a result. The second major inhibition of transformation of alfalfa is its own poor regeneration frequency. Only a few varieties exhibit even modest regeneration, and those elite varieties providing superior performance in the field are notoriously poor regenerators. The combination of these two problems has created a considerable bottleneck in achieving transformation of the plant.

Alfalfa exhibits other traits setting it apart from many crop plants. It is an autotetraploid and is frequently self incompatible in breeding. When selfed, the pollen may not germinate or, when it does, later stops germinating. Thus producing a true breeding parent for hybrids is not possible, which complicates breeding substantially.

It has been determined that there are nine major germplasm sources of alfalfa: *M. falcata*, Ladak, *M. varia*, Turkistan, Flemish, Chilean, Peruvian, Indian, and African. Culture of explant source tissue, such as mature cotyledons and hypocotyls, demonstrates the regeneration frequency of genotypes in most cultivars is only about 10 percent. Seitz-Kris, M. H. and E. T. Bingham, *In vitro Cellular and Developmental Biology* 24 (10):1047-1052 (1988). Efforts have been underway to improve regeneration, and have included attempts at asexual propagation to maintain individual genotypes which possess the regeneration trait. Further, propagation by asexual methods is not practical if many genotypes are involved. Bingham and others have attempted to avoid this problem by recurrent selection. In the first cycle, regenerating genotypes were selected, crossed and recycled until regeneration was improved to 60 percent or better. The result of this was the development of Regen-S, in which two-thirds of the plants were capable of regeneration from callus tissue. E. T. Bingham, et. al., *Crop Science* 15:719-721 (1975).

Additionally, researchers believe that somatic embryogenesis in alfalfa is inheritable, and is controlled by relatively few genes. Efforts at improving regeneration have thus been directed towards isolation of the genetic control of embryogenesis, and breeding programs which would incorporate such information. See, e.g. M. M. Hernandez-Fernandez, and B. R. Christie, *Genome* 32:318-321 (1989); I. M. Ray and E. T. Bingham, *Crop Science* 29:1545-1548 (1989). This is complicated by the characteristics of alfalfa noted above.

This invention relates to improvements in transformation and regeneration of alfalfa by departing from these previous approaches. Direct introduction of DNA is accomplished by the use of microprojectile bombardment. As a result of the use of bombardment, the limitations of *Agrobacterium* are overcome.

Furthermore, limitations in regeneration of alfalfa are overcome by selecting immature cotyledons for transformation and regeneration. It has been found that when immature cotyledons of alfalfa are used, regeneration is considerably improved, and there are no limitations on what type of alfalfa can be regenerated as a result of this method. Thus even elite varieties may be regenerated, and transformed.

Thus, it is an object of this invention to improve transformation rates of *Medicago sativa*.

It is another object of this invention to improve regeneration of *Medicago sativa*.

A still further object of this invention is to allow transformation and regeneration of any variety of *Medicago sativa*.

Still further objects of the invention will become apparent through the following description.

SUMMARY OF THE INVENTION

Microprojectile bombardment is used to transform DNA into *Medicago sativa*, resulting in introduction of DNA into any variety of *Medicago sativa*.

The invention further relates to the use of immature cotyledons of *Medicago sativa* for transformation and regeneration of any variety of *Medicago sativa*.

DESCRIPTION OF THE INVENTION

Microprojectile Bombardment

Figure 1:
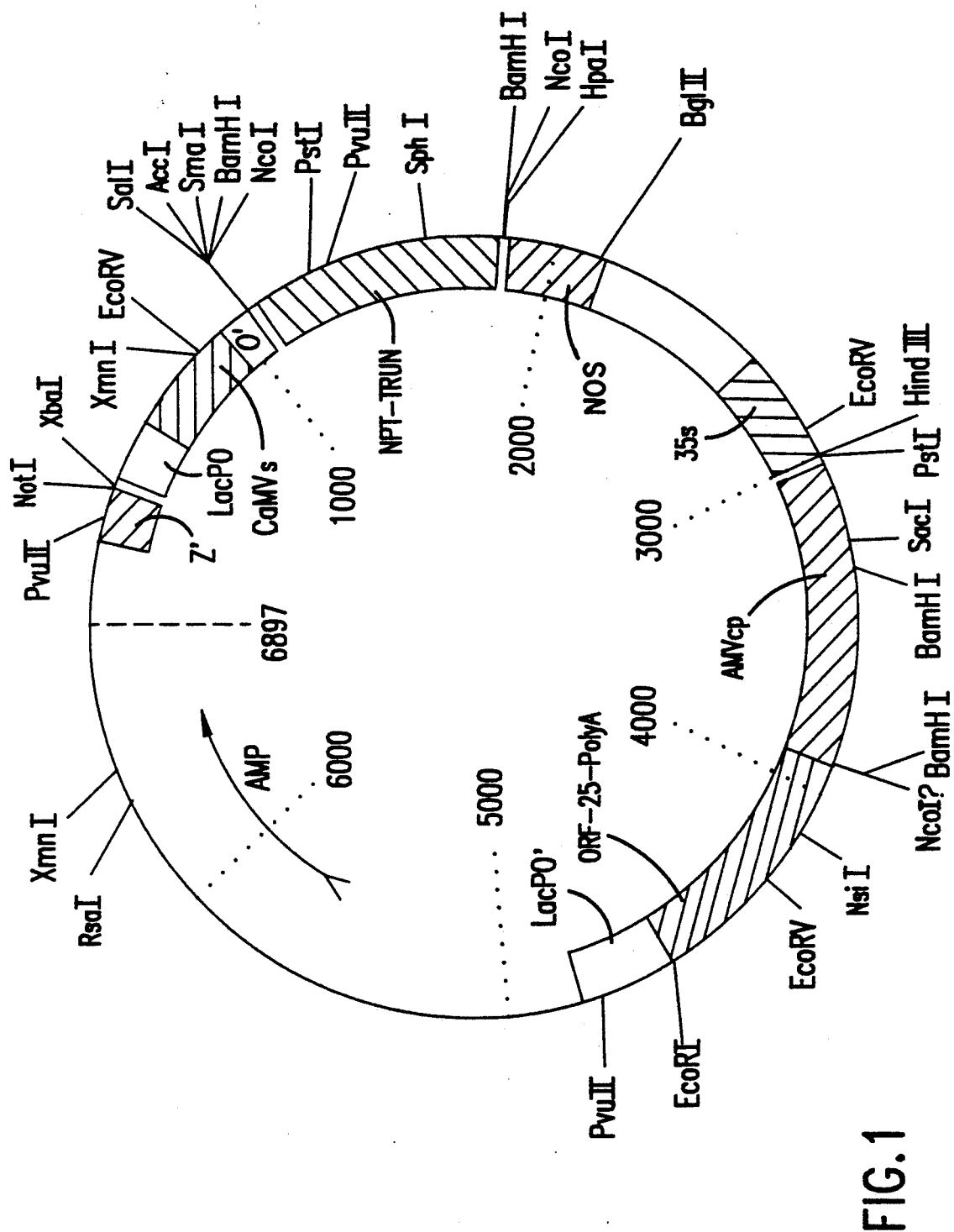
FIG. 1 is a map of plasmid pPHI251.

Microprojectile bombardment in order to transform plant cells is known to those skilled in the art. The general process has been described by T. M. Klein, et al. Proc. Natl. Acad. Sci. USA 85:4305-4309 (1988). This reference, as well as those cited throughout, represent knowledge of those skilled in the art and are each incorporated herein by reference. The basic process includes coating DNA onto small high density particles, microprojectiles, which are then placed into the particle gun or helium gun apparatus and accelerated to a high velocity in order to penetrate plant cell walls and membranes and carry the DNA or other substance into the interior of the bombarded cell.

Klein describes his work as follows: His report describes a process for delivering foreign genes into maize cells that does not require the removal of cell walls and is capable of delivering DNA into embryogenic and nonembryogenic tissues. A plasmid harboring a chimeric chloramphenicol acetyltransferase (CAT) gene was adsorbed to the surface of microscopic tungsten particles (microprojectiles). These microprojectiles were then accelerated to velocities sufficient for penetrating the cell walls and membranes of maize cells in suspension culture. High levels of CAT activity were consistently observed after bombardment of cell cultures of the cultivar Black Mexican Sweet, which were comparable to CAT levels observed after electroporation of protoplasts. Measurable increases in CAT levels were also observed in two embryogenic cell lines after bombardment. Gene expression was observed only when an intron from the alcohol dehydrogenase 1 gene of maize was ligated between the 35 S promoter and the CAT coding region. CAT activity was detected in cell cultures bombarded with microprojectiles with an average diameter of 1.2 um, but not after bombardment with microprojectiles 0.6 to 2.4 um in diameter. Bombarding the same sample several times was found to markedly enhance CAT activity. These results demonstrate that the particle bombardment process can be used to deliver foreign DNA into intact cells of maize.

Plasmids

The plasmids which were used in Klein's study have been described at Callis, J., Fromm, M. and Walbot, V. (1987) *Genes Dev.* 1, 1183–1200.

The plasmid pCaMVI$_1$CN consists of the 35 S promoter from cauliflower mosaic virus, a fragment (BclI/-BamHI) from the alcohol dehydrogenase intron 1 (Adh1), a CAT coding region, and the nopaline synthase polyadenylylation region. The plasmid pCaMVCN is identical to pCaMVI$_1$CN but lacks the ADH1 intron fragment.

Plant Materials

Embryogenic suspension cultures 3-86-17 and 13-217 were derived from type II embryogenic callus (Green, C. E., Armstrong, C. L. & Anderson, P. C. (1983) in *Molecular Genetics of Plants and Animals*, eds. Downey, K., Voellmy, R. M., Fazelahmad, A. & Schultz, J. (Academic, N.Y.), Vol 20, pp. 147). The callus was initiated from a maize inbred designated R21 (for line 3-86-17) or B73 x G35 (for line 13-217). Inbred R21 was derived from a regenerated plant from a long-term callus culture of public inbred B73 and is very similar to B73. Both R21 and G35 are proprietary inbred lines of Pioneer Hi-Bred International (Johnston, Iowa). Suspension cultures of the cultivar BMS were obtained from V. Walbot (Stanford University). Suspension cultures were maintained in Murashige and Skoog (MS) medium (Murashige, T. & Skoog, F. (1962) *Physiol. Plant* 15, 473–497) supplemented with 2,4-dinitrophenol (2 mg/liter) and sucrose (30g/liter). The suspension cultures were passed through a 710-um sieve 7 days prior to the experiment, and the filtrate was maintained in MS medium. In preparation for bombardment with the microprojectiles, cells were harvested from suspension culture by vacuum filtration on a Buchner funnel (Whatman no. 614). The same cell batch from each genotype was used within each experiment.

Particle Bombardment of Suspension Cultures

The particle gun device and general methods for bombardment of cells with microprojectiles have been described (Sanford, J. C., Klein, T. M., Wolf, E. D. & Allen, N. (1987) *Particle Sci. Technol*, 5, 27–37 and Klein T. M., Wolf, E. D., Wu, R. & Sanford, J. C. (1987) *Nature (London)* 387,70–73). Before bombardment, cells (100 mg fresh weight) were placed in a 3.3-cm Petri dish. The cells were dispersed in 0.5 ml of fresh culture medium to form a thin layer of cells covered by a film of medium. The uncovered Petri dish was placed in the sample chamber and a vacuum pump was used to decrease the pressure in the chamber to 0.1 atm=101.3 kPa) (operation in a partial vacuum allows the microprojectiles to maintain their velocity over a longer distance, since air resistance is an important factor in their deceleration).

Unless otherwise noted, the cells were bombarded with tungsten particles with an average diameter of 1.2 um (GTE Sylvania) or 2.4 um (General Electric). Plasmid DNA was absorbed to the microprojectiles by adding 5 ul of DNA (1 ug per ul of TE buffer, Ph 7.7; 0.1M) to 25 ul of a suspension of tungsten particles (0.05 g per ml of distilled water) in a 1.5-ml Eppendorf tube. Cacl$_2$ (25 ul of 2.5M solution) and spermidine free base (10 ul of 0.1M solution) were then added to the suspension. Particles became agglomerated and settled to the bottom of the Eppendorf tube=10 min after addition of CaCl$_2$ and spermidine. Most of the supernatant (45 ul) was then removed and the particles were deagglomerated by briefly (1 sec) touching the outside of the Eppendorf tube to the probe (horn type) of a sonicator (Heat System/Ultrasonics, Plainview, N.Y.). Five microliters of the resulting suspension of microprojectiles was then placed on the front surface of a cylindrical polyethylene macroprojectile. The macroprojectile was then placed into the barrel of the particle gun device and a blank gun powder charge (no. 1 gray extra light; Speed Fasteners, Saint Louis) was loaded into the barrel behind the macroprojectile. A firing pin device was used to detonate the gun powder charge, accelerating the macroprojectile down the barrel of the device where it impacts with a stopping plate. Upon impact, the microprojectiles are propelled from the front surface of the macroprojectile and continue toward the cells through a small aperture in the stopping plate. The cells were positioned 15 cm from the end of the barrel of the particle gun. After bombardment, the Petri dish was removed from the apparatus and the cells were transferred to 5 ml of fresh medium in a 15-ml polypropylene tube. The cells were then maintained in this tube with agitation at 27° C. until harvested for analysis. Controls consisted of cells bombarded with microprojectiles lacking DNA.

In one set of experiments, the cells were treated either with a medium of high osmotic potential or with a mixture of medium and mineral oil during bombardment. In the first case, 100 mg of BMS cells were dispersed in 0.5 ml of MS medium supplemented with mannitol (0.4M), 30 min prior to bombardment. After particle bombardment, the cells were left in the mannitol-containing medium for an additional 30 min, after which they were resuspended in 5 ml of standard MS medium. In the second case, the cells were dispersed in an emulsion of either 0.1 ml of sterile mineral oil and 0.5 ml of MS medium, 0.2 ml of mineral oil and 0.4 ml of MS medium, or 0.6 ml of MS medium lacking mineral oil. After bombardment, the cells were suspended in 5 ml of MS medium.

CAT Assays. Analyses of CAT activity were performed 96 hr after bombardment. Tissue extracts were prepared by sedimenting the cells at=13,000×g for 10 min in a 1.5-ml Microfuge tube. The supernatant was removed and 100 ul of buffer (0.25M Tris-HCl, pH 7.8) was added to the pellet. The sample was homogenized on ice for=2 min with a disposable polypropylene pestle (Kontes) driver at 300 rpm by an electric motor.

After grinding, the sample was Vortex mixed briefly to complete the extraction of soluble protein. Cell debris was removed by centrifugation at 13,000×g in a Microfuge at 4° C. for 10 min. The supernatant was decanted and normalized to a volume of 200 ul with the Tris-HCl buffer.

The CAT activity in the extracts was determined as reported (Gorman, C. M., Moffat, L. F. & Howard, B. H. (1982) *Mol. Cell. Biol.* 2, 1044-1051) except the samples were heated at 60° C. for 12 min before addition of substrates. The reaction mixture was incubated for 1.5 hr. at 37° C., and reaction products were extracted from the mixture with 300 ul of cold ethyl acetate, air dried, and resuspended in 20 ul of ethyl acetate for spotting on TLC plates (Baker, Phillipsburg, N.J.). After TLC resolution of chloramphenicol and its acetylated derivatives by using chloroform/methanol (95:5), autoradiograms of the TLC plates were made (60-hr exposure at 22° C.; Dupont Cronex film).

Quantitative results were obtained by scintillation counting of separated spots of chloramphenicol and its acetylated derivatives, and the percentage conversion to acetylated products was calculated. CAT activity (1 unit of CAT catalyzes the acetylation of 1 ng of chloramphenicol per min at 37° C.) was determined by comparison with a standard curve of acetylation conversions obtained with purified bacterial CAT (P-L Biochemicals). Protein in the cell extracts was determined according to Bradford (Bradford, M. M. (1976) *Anal. Biochem.* 72, 248-254). CAT activity was standardized on the basis of units of CAT activity per mg of soluble protein.

Obviously, there may be numerous modifications to this basic process, but Klein describes at least one method of accomplishing microprojectile bombardment.

Previous work involved delivery of foreign genes through this method into intact plant of tobacco tissue, but its application to the economically important species alfalfa has not been successfully accomplished. Tomes, et al. *Plant Molecular Biology* 14:261-268 (1990). Microprojectile bombardment of alfalfa to achieve transformation has not been previously reported.

Introduction of DNA into a plant is demonstrated at first by transient expression. Short term expression is noted by confirming the presence of the DNA within the plant cells 24 to 48 hours after bombardment. When expressed up to 72 hours after bombardment it is demonstrated that the DNA has been delivered via the particle gun or other method and that the DNA vector functions. When continuing to be expressed two to eight weeks after bombardment, it may be concluded the DNA is persistent and likely integrated into the plant genome. Its ability to persist at this point shows it has survived attack from nucleases which typically would attack unprotected foreign DNA. When the $R_o$ plants are recovered, continuing expression is further indication that stable transformation into the plant cells has occurred. Southern analysis allows confirmation of this. When crossed and the $R_1$ generation analyzed, expression and inheritibility of the DNA is further confirmed.

A variety of plant cell sources can be used for transformation by microprojectile bombardment. Hypocotyls, cotyledons of mature seed and petioles are plant tissue which can be subjected to bombardment. The applicant has discovered that when cotyledons are used, satisfactory transformation results. While not wishing to be bound by any theory, it is proposed that cotyledons may be a better source of tissue for bombardment because the cells to be bombarded are those which are capable of giving rise to plants. Mature cotyledons are also convenient sources of tissue and easy to excise from the seed.

Cotyledons from mature seed can be used in transformation, that is, seed which has reached dormancy. This seed is then placed in water, typically for one to several days, the root breaks through the seed coat, and the cotyledon is dissected. The use of immature cotyledons is discussed more fully below.

It has been found that the optimum stage for best transformation results of mature cotyledons occurs when bombarded after 24 to 120 hours of imbibing water. It has been discovered that at this point regeneration, transient transformation, and resulting transformation is at its optimum. Prior to 24 hours it is as a practical matter more difficult to remove the seed coat without damaging the cotyledon. After 120 hours, it is more difficult to regenerate the plants.

The tissue should be bombarded one or two times, and bombardments in excess of this would likely kill the cells.

Tissue culture was also optimized for the maximum regeneration possibilities. In the experiments described below, Regen-S, was used. As noted supra, Regen-S is known for its improved regeneration potential. Set forth below are tissue cultures which were employed. The most important factor in tissue culture optimized for regeneration is high concentration of 2,4-dichlorophenoxyacetic acid (2,4-D) as compared to a low concentration of kinetin. Tissue/organ culture is described generally by Atanassov and Brown in *Plant Cell Tissue Organ Culture* 4:111-122 (1985).

CULTURE MEDIA

The following describes media used in regeneration of transformed and non-transformed alfalfa. It is to be understood that those skilled in the art could use media which varies considerably from these media and fall within the scope of the invention. The description is given by way of example.

Gamborg's Based Medium

Gamborg's B-5 medium is a widely used medium for culture of plant species. It is well known to those skilled in the art and is described in detail at O. L. Gamborg, R. A. Miller, K. Ojima, *Exp. Cell. Res.* 50:151-158 (1968). It forms a component of media listed below.

Modified B5 Medium

This medium is described at Atanassov, A. and Brown, D. C. W. *Plant Cell Tissue and Organ Culture* 3:149-162 (1984). A typical mixture is that formulated by GIBCO Laboratories and include: 1 mg/l 2,4-D, 0.2 mg/l kinetin, 30 g/l sucrose, 3000 mg/l $KNO_3$, 895 mg/l $CaCl_2$, 800 mg/l l-glutamine, 500 mg/l $MgSO_4$ $7H_2O$, 100 mg/l serine, 10 mg/l L-glutathione, 1 mg/l adenine, with the modification that was used instead of gelrite reported in Atanassov, 9 g/l bacto agar. It forms a component of media listed below.

MS Medium

This medium is well known to those skilled in the art and is described in detail at T. Murashige and F. Skoog, *Physiologia Plantarum* 15:473-497 (1962). A typical mixture is that formulated by Gibco Lab and includes:

| Component | mg/L |
|---|---|
| $NH_4NO_3$ | 1650.0 |
| $KNO_3$ | 1900.0 |
| $CaCl_2.2H_2O$ [a] | 440.0 |
| $MgSO_4.7H_2O$ [b] | 370.0 |
| $KH_2PO_4$ | 170.0 |
| $Na_2.EDTA$ | 37.3 |
| $FeSO_4.7H_2O$ | 27.8 |
| $H_3BO_3$ | 6.2 |
| $MnSO_4.H_2O$ | 16.9 |
| $ZnSO_4.7H_2O$ | 8.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |

Blaydes Medium and Modifications

This well known medium to those skilled in the art is described in detail at D. F. Blaydes, *Physiol. Plant.* 19:748–753 (1966).

BO (basal Blaydes medium) contains per liter: 300 mg $KH_2PO_4$, 100 mg $KNO_3$, 1 g $NH_4NO_3$, 347 mg Ca(-$NO_3$)$_2$ 4 $H_2O$, 35 mg $MgSO_4$ 7 $H_2O$, 65 mg KCl, 0.8 mg KI, 1.5 mg $ZnSO_4$ 7 $H_2O$, 1.6 mg $H_3BO_3$, 4.4 mg $MnSO_4 H_2O$, 2 mg glycine, 0.1 mg thiamine hydrochloride, 30 g sucrose, 10 g (5.57 g $FeSO_4;7H_2O$ in 500 ml hot distilled water with 7.45 g Na2EDTA in 500 ml hot distilled water with pH to 5.9–6.0.

BII medium is the same as BO, but contains 2 mg/l each NAA, Kinetin, and 2,4-D.

BOi2Y is the same as BO, but contains 100 mg/l inositiol and 2 g/l bacto yeast extract. After embryo induction, explants must be removed from exposure to 2,4-D. 2,4-D appears to inhibit embryo development.

Schenk and Hildebrandt (SH) medium

This medium is well known to those skilled in the art and is described in detail at B. V. Schenk and A. C. Hildebrant, *Can. J. Bot.* 50:199–204 (1975). SHII contains 9.05 uM 2,4-dichlorophenoxy acetic acid (2,4-D) and 9.30 uM kinetin Modified SH medium This medium is well known to those skilled in the art and is described in detail at D. H. Mitten, S. J. Sato, and T. A. Skokut, *Crop Sci.* 24:943–945 (1984). Modified SH medium contained: 25 uM α-naphthaleneacetic acid (NAA) and 10 uM kinetin, callus was transferred to SH medium containing 50 uM 2,4-D and 5 uM kinetin, transferred 3 days later to regeneration medium containing BOi2Y.

The following is presented merely as examples and are not intended to limit the scope of the invention.

Figure 2:
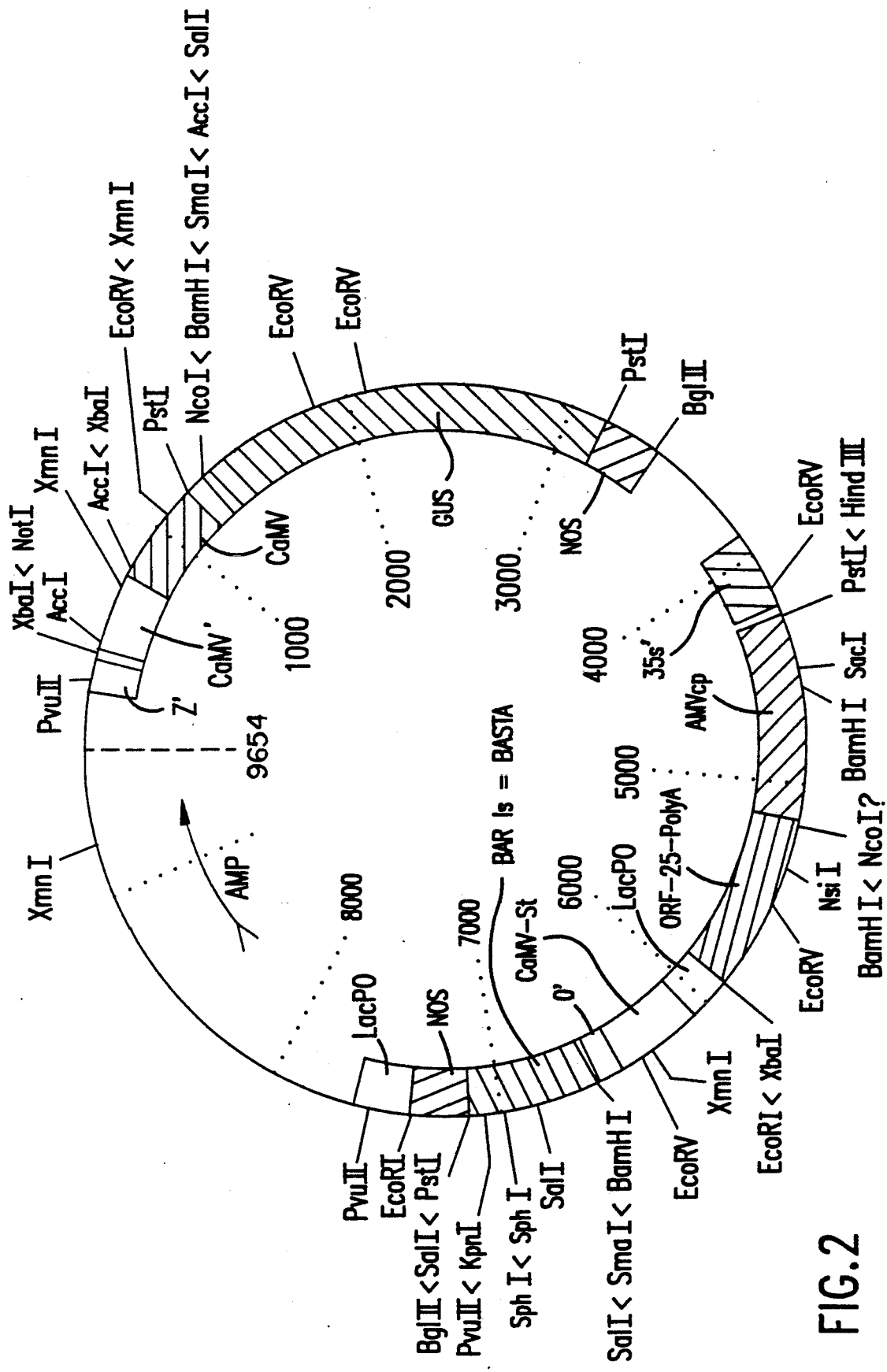
FIG. 2 is a map of plasmid pPHI256.

In each of the experiments set forth below, Regen-S, as described above, was employed. This variety is known for its high regeneration potential. Genes encoding the Alfalfa Mosaic Virus coat protein (AMVcp), Phosphinotricin Acetyl Transferase (referred to here as BAR), Neomycin Phosphotransferase (NPTII) and β-glucuronidase (GUS), were transformed into this genotype using a DuPont PDS 1000~ particle gun. The alfalfa mosaic virus coat protein may protect plants from AMV pathogens, BAR inactivates the nonselective herbicide phosphinotricin, present in Basta ® medium and NPTII inactivates kanamycin. Plasmid pPHI251 encoding for NPTII, and AMVcp was used. A map of this plasmid is shown in FIG. 1. Plasmid pPHI256 was separately used as indicated below in coding for BAR, AMVcp, and GUS. A map of this plasmid is found at FIG. 2.

EXPERIMENT 1

Alfalfa Mature Cotyledon Particle Gun Transformation on Basta ® Selection

Explant: Mature Cotyledons of RegenS
Plasmid: pPHI256 (GUS, AMVcp, BAR)
Bombardment: 8 cotyledons per plate (8 plates) bombarded twice with 1.8 um tungsten particles
Culture: Seed germinated 2 days and embryonic axis removed from cotyledon Cotyledon plated to filters soaked with 0.25M sorbitol and adaxial surface bombarded twice Cultured on modified B5 medium 2 days 3 day post-bombardment cotyledons cultured on a modified B5 medium containing 2.5 mg/l Basta ® for 9 wks
4 wks callusing/embryogenesis (B5 base, 1 mg/l 2 4-D and 0.2 mg/l kinetin)
2 wks embryogeny/embryo development (B5 base, 0.1 mg/l NAA)
3 wks embryo maturation (Boi2Y base, no hormones)
Rooted on 5 mg/l Basta ® Shoot tips cultures initiated
Results:
60 embryos recovered
11 browned and died during selection
10 abnormal sacrificed for GUS histochemical staining (all negative)
31 abnormal recultured for callus (also GUS negative)
8 normal—5 survived higher selection In this experiment, five plants were recovered from culture of bombarded mature cotyledons on modified B5 media containing 2.5 mg/l Basta ®. Each plant was identified to contain the AMVcp and BAR genes by the method of polymerase chain reaction amplification, as shown in Table 1. β-glucuronidase enzyme activity was also identified in the five plants by a GUS assay described by Rao, G. and Flynn, P., *BioTechniques*, Vol. 8, No. 1, pp. 38–40 (1990).

TABLE 1

| Alfalfa Plants Recovered on Basta ® Selection | | | | | |
|---|---|---|---|---|---|
| | | | GUS[a] | | |
| | | | Shoot | | Root |
| | PCR | | Assay | Assay | Assay | Assay |
| Plant | AMVcp[b] | BAR[c] | 1 | 2 | 1 | 2 |
| E1 | + | + | 3 | — | 2 | 2 |
| E2 | + | + | — | — | 2 | 1 |
| E3 | + | + | — | 1 | — | N/A |
| E4 | + | + | 2 | — | — | N/A |
| E5 | + | + | — | — | — | — |

[a]Fluorometric GUS assay expressed as pg/μg total protein.
[b]Oligonucleotides target internal to AMVcp coding region.
[c]Oligonucleotides target CaMV promoter and 5' region of BAR coding region.

Below, PCR analysis of the parent and progeny is set forth showing 50% were positive for BAR. The first three plants are progeny followed by a maternal plant showing BAR expression, a paternal negative control, maternal plant positive for BAR and controls.

TABLE 2

| PCR Analysis of Parent and Progeny Plants | | | |
|---|---|---|---|
| Sample | Source | BAR | AMV |
| BOO1E2 × YAE92 | Progeny | + | — |
| BOO1E2 × YAE92 | Progeny | — | — |
| BOO1E3 × YAE92 | Progeny | — | — |
| Maternal BOO1E2 | Maternal | + | — |
| YAE92 Paternal | Paternal | — | — |

TABLE 2-continued

| | PCR Analysis of Parent and Progeny Plants | | |
|---|---|---|---|
| Sample | Source | BAR | AMV |
| Maternal BOO1E3 | Maternal | + | − |
| RA3 11-5 + control[a] | NPTII+ AMV+ | − | + |
| RA3 C308 − control | | − | − |

[a] A description of this positive control is found at Hill, et al., Bio/Technology, 9:373–377 (1991).

Southern analysis was performed on the parent plants which were found to be clones and were positive by PCR for BAR and AMVcp genes. Thus, it can be seen heritable transformation of plants was achieved.

In summary, it can be seen that transformation of mature cotyledons from alfalfa can be accomplished through he use of microprojectile bombardment. However, as noted, regeneration is typically poor. Regeneration is dramatically improved by the use of immature cotyledons in transformation and regeneration.

Immature Cotyledons

Somatic embryogenesis can be direct, where embryos are formed directly from the cells, or indirect where a callus is formed which goes through dedifferentiation.

Where in the past research has centered on using a particular germplasm source, selecting for genotypes with improved regeneration, recurrent selection to create varieties having improved regeneration, or selection for genes in plant breeding techniques in developing improved regeneration lines, this invention uses an entirely different approach. See, e.g., Mitten, et al., *Crop Science*, 24:943 (1984); Seitz, Kris & Bingham, In Vitro, 24:1047 (1988); Brown and Atanassov, *Plant Cell Tissue Organ Culture*, 4:111–122 (1985). Thus, the invention relates to the use of immature cotyledons to improve regeneration, and thereby transformation of alfalfa.

The use of immature cotyledons has been found to be an important factor in regeneration. As a seed develops, from about 0–5 days past pollination the seed embryo is globular in shape and generally without form, translucent in color. At about 5 days it demonstrates a heart shaped appearance. The embryo then undergoes rotation, and at about 10 days has a visible cotyledon. The color is translucent to light green, and a scalpel placed behind the cotyledon can almost be visualized. At about 15 days the differentiation of the seed parts has become more distinct, and by 20 days it has a dark green appearance. Beyond 25 days, the dark green color gives away to a yellowing. At 30 days it is creamy white in color. It is at this point that the dormancy process is underway.

It has been found by the applicant that immature cotyledons providing improved regeneration include those which are formed up to 25 days past pollination. At 5–7 days post-pollination the heart stage is apparent, however, as a practical matter it is difficult to excise the cotyledon portion at this stage and to differentiate it from the other parts of the embryo. The cotyledon can be harvested more easily beginning at about 10 days when it has a translucent to very light green color. The time period between 10–15 days is preferred and provides for considerably improved regeneration results.

The most preferable time to excise the cotyledon is at about 10 days past pollination and/or the cotyledon has a translucent to light green color. The light green color can be compared to that found at Panton Color Chart Number PMS372.

As a result of using immature cotyledons as provided herein, it is possible to regenerate varieties which have never been capable of transformation and regeneration before. Thus, while highly regenerable plants in the past have not always carried the preferred phenotypes, now one may regenerate even elite lines of alfalfa. These elite lines typically have desirable production qualities but notoriously poor regeneration.

As a further result, when immature cotyledons are used, one can obtain transformation of such elite lines which could not be regenerated previously after introduction of DNA. The transformation may occur by bombardment or the previously known use of agrobacteria, with regeneration now possible.

EXPERIMENT 2

The typical protocol includes placing the immature cotyledon explant on a modified B5 medium. After 21–28 days somatic embryos are transferred to MS medium and allowed to mature. Obviously there are a number of variations on this protocol known to those skilled in the art and this is given by way of example. The following shows improved regeneration which correlates to explant age.

Figure 3:
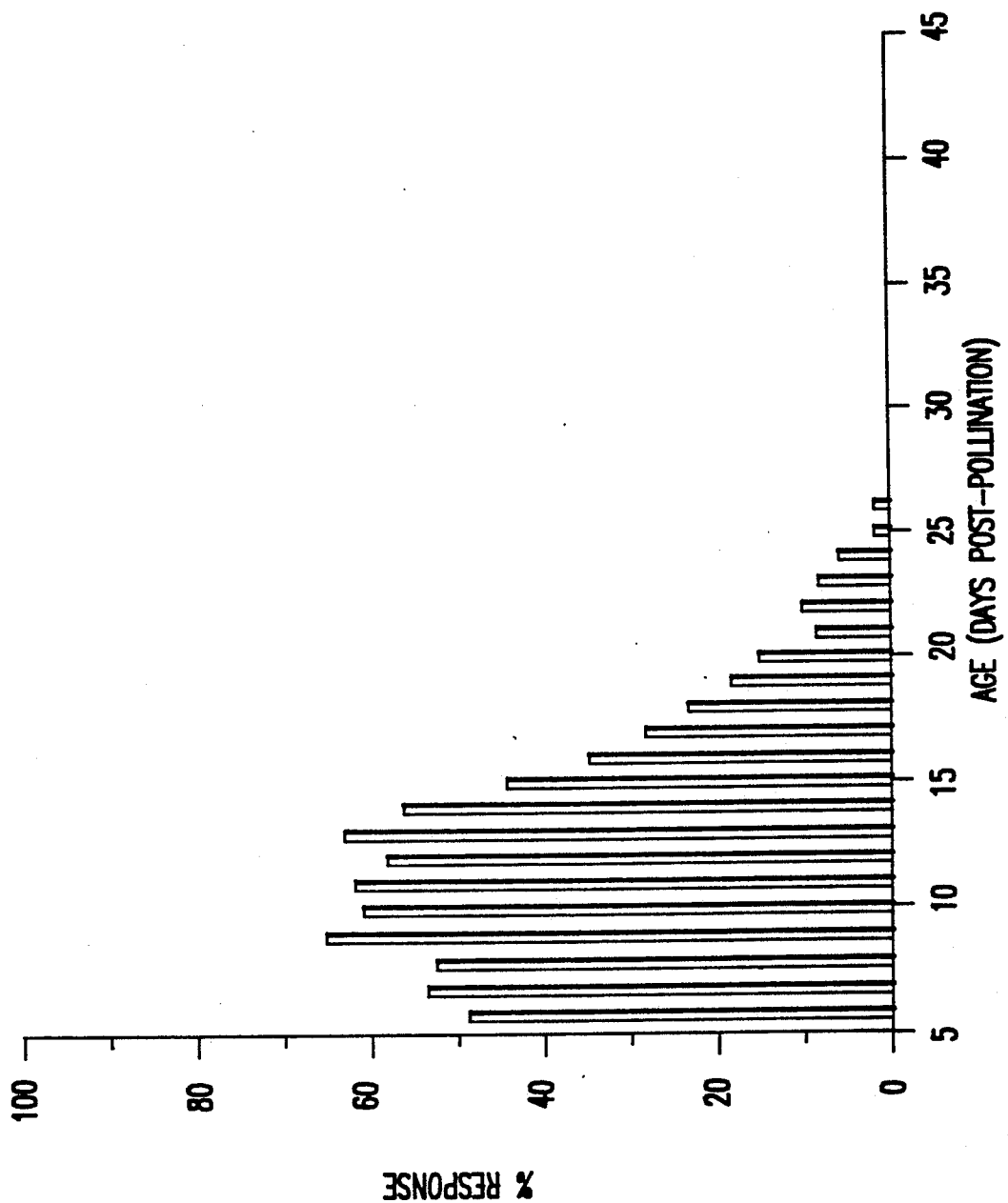
FIG. 3 is a graph showing time course harvest results plotting age of the cotyledon on the x axis and regeneration response on the y axis.

Plants from two varieties were divided into three groups. Six plants from YAE92 were placed into a first group, five plants from YAE92 were placed into a second group, and five plants from YAM93 were placed into a third group. Table 3 below shows the background of each variety. Each group was crossed exclusively within itself. From the resulting plants, each raceme is individually identified and its integrity maintained. Harvesting occurs at timed intervals from 0–30 days past pollination, with an early harvest from a numbered raceme and later harvest from the same raceme. By maintaining the integrity of the group and harvesting from a numbered raceme over the time course of the experiment, it can be demonstrated that variation of genotype even within a particular variety does not affect regeneration as long as regeneration is from immature cotyledon. Each of the cotyledons excised at the time course harvest was regenerated. A graph at FIG. 3 of the results plots the age of the cotyledon post-pollination on the x-axis and the regeneration response on the y-axis. The results show that even from the same raceme there is increasing regeneration beginning at just after pollination, up to about 15 days past pollination, with declining regeneration up to maturity.

The scoring and evaluation of the time course harvest is shown in Table 4. Thus, it is clear that age of the cotyledon excised is the critical factor effecting regeneration.

TABLE 3

| | Percent Contribution of Germplasm | | | | | | | | | |
|---|---|---|---|---|---|---|---|---|---|---|
| | varia | ladak | turk | falc | chil | peru | indian | african | flemish | unk. |
| YAE92 | 27 | 8 | 4 | 6 | 8 | — | — | — | 47 | — |
| YAM93 | 23 | 8 | 10 | 8 | 7 | 2 | — | — | 42 | — |

TABLE 4

Regeneration Shown as Percent Response, From Immature Cotyledons of Different Ages From Controlled Matings Within Three Groups of Alfalfa Plants

| AGE Days Post-Pollination) | Number Cotyledons Evaluated | Percent Response |
| --- | --- | --- |
| 6 | 44 | 48. |
| 7 | 38 | 53. |
| 8 | 42 | 52. |
| 9 | 39 | 64. |
| 10 | 52 | 60. |
| 11 | 44 | 61. |
| 12 | 51 | 57. |
| 13 | 53 | 62. |
| 14 | 38 | 55. |
| 15 | 42 | 43. |
| 16 | 38 | 34. |
| 17 | 42 | 27. |
| 18 | 49 | 22. |
| 19 | 59 | 17. |
| 20 | 56 | 14. |
| 21 | 30 | 7. |
| 22 | 45 | 9. |
| 23 | 41 | 7. |
| 24 | 19 | 5. |
| 25 | 68 | 1. |
| 26 | 73 | 1. |
| 27 | 18 | 0. |
| 28 | 9 | 0. |
| 29 | 17 | 0. |
| 30 | 17 | 0. |
| 31 | 15 | 0. |
| 32 | 11 | 0. |
| 33 | 15 | 0. |
| 34 | 9 | 0. |
| 35 | 10 | 0. |
| 36 | 17 | 0. |
| 37 | 18 | 0. |
| 38 | 14 | 0. |
| 39 | 11 | 0. |
| 40 | 12 | 0. |

Thus, it can be seen that when immature cotyledons are used in regeneration of alfalfa, dramatically improved results occur.

EXPERIMENT 3

This experiment confirms that it is the immature cotyledon use which provides for the improved regeneration and may be applied to any germplasm source. A number of varieties, including those that have poor or little regeneration were regenerated using immature cotyledons. A minimum of twelve plants of each of the varieties listed in Table 5 were planted and pollinated, with the exception that 15 plants of Grimm (Pi 452472), 30 plants of Mesa Sirsa and 1 plant of RA3 clone were planted and pollinated. Each raceme identified was harvested at about 10–15 days past pollination and at maturity (about 30 days). Immature and mature cotyledons were regenerated as described in Experiment 2.

Figure 4:
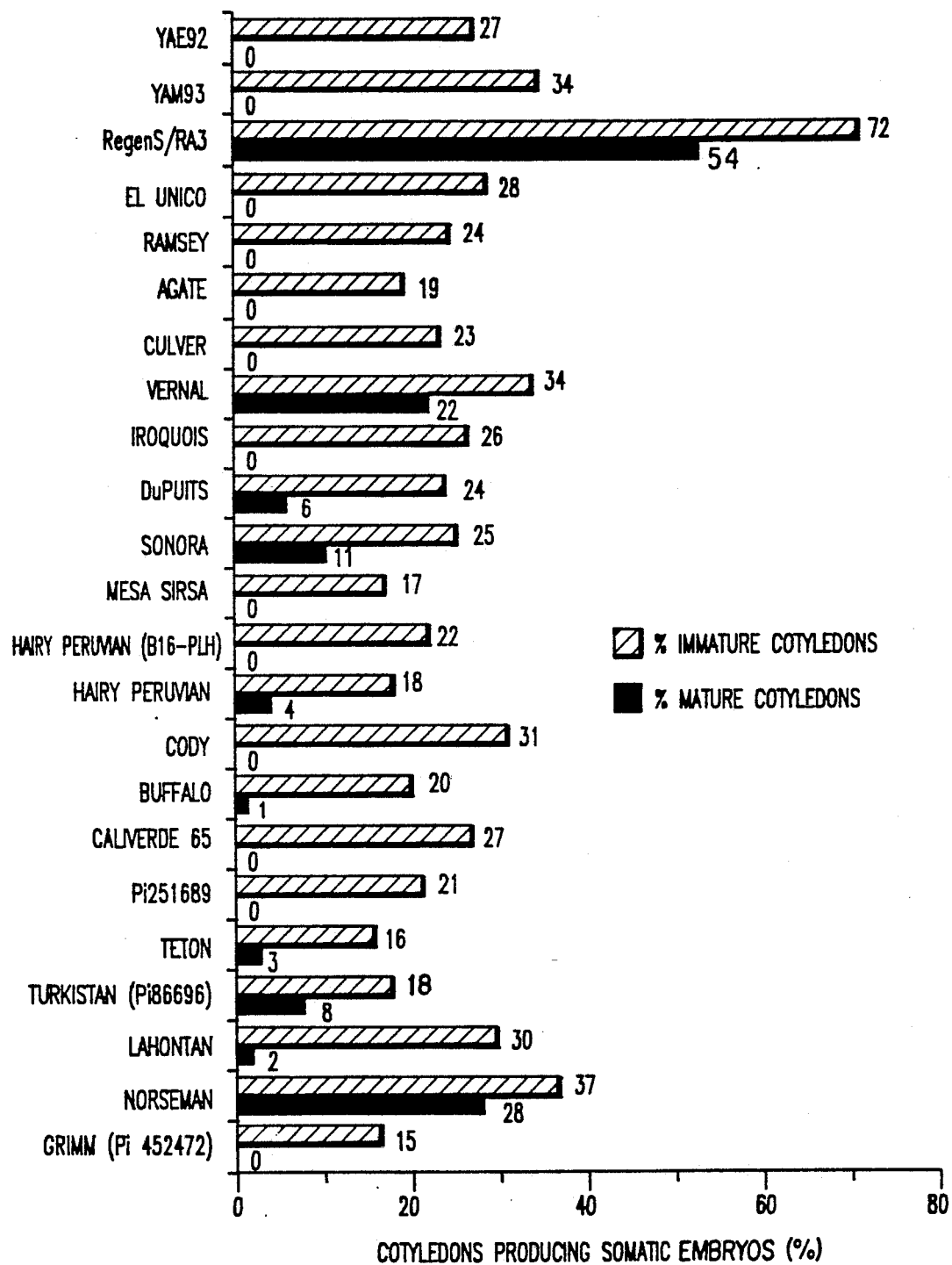
FIG. 4 is a graph of regeneration using immature cotyledons hashed and mature cotyledons (solid bar) of varieties listed.

The data in Table 5 below demonstrates that use of immature cotyledons substantially improves regeneration even in those varieties which traditionally have poor or no regeneration. FIG. 4 graphically displays the differences in regeneration occurring in varieties that are extremely difficult to regenerate. Selected varieties and, in particular, those with the worst regeneration, are shown in terms of percent regeneration of mature cotyledons in the solid bar; and percent regeneration of immature cotyledons, represented by the hashed bar. Use of immature cotyledons resulted in improved regeneration in each instance, including those varieties with no regeneration using mature cotyledons.

TABLE 5

Comparison of Percent of Regeneration of 30 Days Past Pollination Mature Cotyledons With Percent Regeneration of 10-15 Day Post-Pollination Immature Cotyledons

| ALFALFA DESIGNATION | # MATURE COTYLEDONS SAMPLED | % MATURE COTYLEDONS REGENERATING | # IMMATURE COTYLEDONS SAMPLED | % IMMATURE COTYLEDONS REGENERATING |
| --- | --- | --- | --- | --- |
| Grimm (Pi 452472) | 206 | 0 | 223 | 15 |
| Norseman | 152 | 28 | 198 | 37 |
| Lahontan | 167 | 2 | 184 | 30 |
| Turkistan (Pi 86696) | 176 | 8 | 186 | 18 |
| Teton | 145 | 3 | 175 | 16 |
| Pi251689 | 140 | 0 | 129 | 21 |
| Caliverde 65 | 138 | 0 | 167 | 27 |
| Buffalo | 127 | 1 | 158 | 20 |
| Cody | 161 | 0 | 183 | 31 |
| Hairy Peruvian | 147 | 4 | 166 | 18 |
| Hairy Peruvian (B16-PLH) | 150 | 0 | 173 | 22 |
| Mesa Sirsa | 243 | 0 | 262 | 17 |
| Sonora | 110 | 11 | 127 | 25 |
| DuPuits | 138 | 6 | 145 | 24 |
| Iroquois | 143 | 0 | 158 | 26 |
| Vernal | 152 | 22 | 161 | 34 |
| Culver | 170 | 0 | 173 | 23 |
| Agate | 135 | 0 | 155 | 19 |
| Ramsey | 121 | 0 | 181 | 24 |
| El Unico | 149 | 0 | 190 | 28 |
| RegenS/ RA3 | 43 | 54 | 63 | 72 |
| YAM93 | 164 | 0 | 196 | 34 |
| YAE92 | 179 | 0 | 187 | 27 |

EXPERIMENT 4

Three separate tests were conducted to determine if immature embryos could be transformed.

Figure 5:
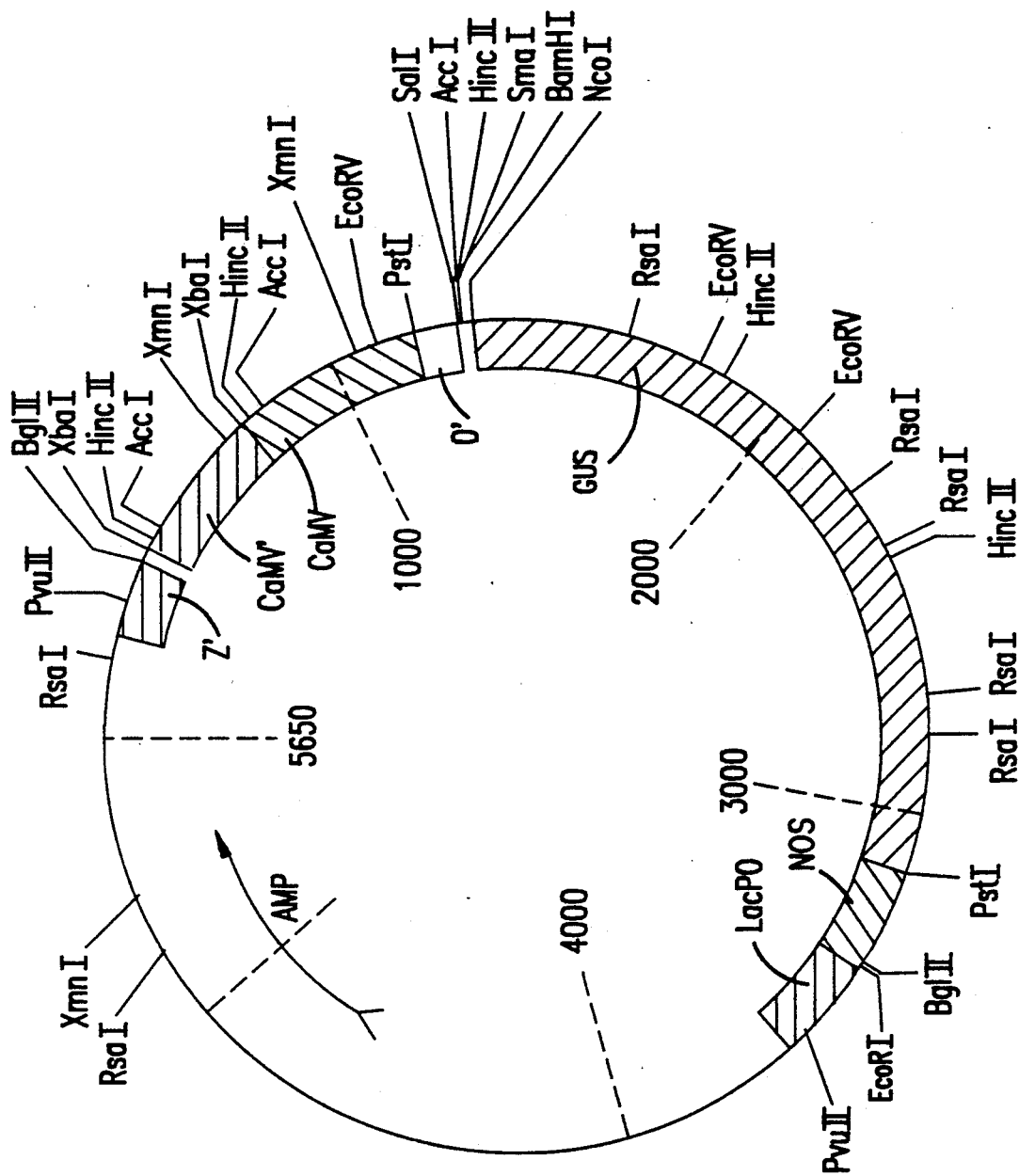
FIG. 5 is a map of plasmid pPHI413.

In the first test, cotyledons were bombarded with pPHI413 (see FIG. 5), as above, and levels of GUS expression assayed. Forty-two samples were bombarded. Optimum expression occurred 48 to 72 hours post bombardment where 26 of the 42 samples expressed GUS with a mean of 1.7 pg/μg total protein. Five days post bombardment 6 of 30 samples showed an average of 2 pg/μg total protein, while at 17 days post bombardment 3 of 30 samples showed an average of 2 pg/μg total protein.

In the second, the effect of bombardment on alfalfa regeneration under selection was studied. Immature cotyledons of Regen S were harvested 11 days post-pollination. Cotyledons were excised from the embryo, bombarded three times with the plasmid pPHI251 (FIG. 1), adsorbed to tungsten particles, and cultured on modified B5 media containing 25 mg/l kanamycin sulfate. Somatic embryos were harvested approximately two months after treatment, allowed to desiccate on MS media for two months, and germinated on MS media containing 100 mg/l kanamycin sulfate. Leaf tissue was harvested and assayed for neomycin phosphotransferase (NPTII) activity. The results are shown in Table 6.

TABLE 6

| Plant | NPTII activity pg/μg total protein | AMVcp (elisa) |
| --- | --- | --- |
| CBX106 | 3 | + |
| CBX107 | 2 | − |
| CBY107 | 5 | − |
| CBY108 | 4 | − |
| CBZ108 | 1 | − |
| CBX112 | 1 | + |
| CBY112 | 3 | − |
| CBZ112 | 1 | − |
| CBA112 | 1 | − |
| CBX115 | 2 | − |
| CBX116 | 2 | + |
| CBY116 | 3 | − |
| CBX117 | 3 | − |
| 1 Regen S 3-11 | 13 | − |
| 2 Regen S 3-11 | 10 | − |
| 3 Regen S 3-11 | 9 | − |
| Regen S Negative Control[a] | 0 | − |
| Rambler Positive Control[b] | 4 | + |

[a]The negative control was bombarded with TE buffer-treated tungsten particles and regenerated on media not containing kanamycin.
[b]Rambler Positive Control was a previously identified transgenic alfalfa plant shown to contain and express the neomycin phosphotransferase gene (Hill et al., Bio/Technology, 9:373-377 (1991)).

In the third test, yet another embodiment of the invention is demonstrated and the affect of bombardment on the regeneration of transformed elite alfalfa varieties was examined. Immature cotyledons were excised from 11 day post-pollination embryos. Somatic embryos were regenerated. Somatic embryos were bombarded five times with tungsten particles adsorbed with the plasmid pPHI251 (FIG. 1) and cultured on modified B5 media containing 25 mg/l kanamycin sulfate. Embryos were subcultured at 20 days post-bombardment to fresh modified B5 media containing 25 mg/l kanamycin sulfate. Green somatic embryos were harvested 50 days post bombardment and matured on MS medium containing 100 mg/l kanamycin sulfate. Leaf samples were taken at 80 days post-bombardment and assayed for neomycin phosphotransferase activity. The results are shown in Table 7.

TABLE 7

| Yam93 Regenerant | NPTII Activity (pg/μg Total Protein) |
| --- | --- |
| CB93.1 | 11 |
| CB93.2 | 13 |
| CB93.3 | 3 |
| CB93.4 | 8 |
| CB93.5 | 4 |
| CB93.6 | 9 |
| Yam93 negative control[a] | 0 |
| Rambler 10-1-1[b] | 2 |

[a]The negative control plant was regenerated from bombarded immature cotyledons bombarded with TE-buffer treated tungsten particles.
[b]Rambler 10-1-1 was a previously identified transgenic plant shown to contain and express the neomycin phosphotransferase gene. [Hill, et al., Bio/technology, 9:373-377 (1991)].

The latter test demonstrates that when immature cotyledons are used to form somatic embryos, and then those embryos are bombarded, even more plants are recovered. Furthermore, the resulting plant has been found to retain this ability to regenerate. Elite varieties can not only be regenerated, but also retain this property.

It can further be seen that bombardment of the immature embryos or somatic embryos does not adversely affect regeneration and that DNA is expressed in these now regenerable cells and plants.

The foregoing demonstrates transformation of Medicago sativa, transformation with particle acceleration, and that substantially improved regeneration of Medicago sativa is possible by the use of immature cotyledons. Regeneration of varieties not previously regenerated or with very poor regeneration is achieved. Thus, transformation of these same varieties is now possible.

Thus, it can be seen the invention accomplishes its objectives.

We claim:

1. A process of obtaining expression of foreign DNA in cells of alfalfa comprising:
    attaching the foreign DNA to carrier particles;
    physically accelerating the particles at the cells to bombard cells of immature cotyledons six to 25 days past pollination with the particles having the foreign DNA such that at least some of the foreign DNA is inserted into the interior of at least some of the cells; and
    confirming expression of the foreign DNA in the cells.

2. The process of claim 1 wherein the foreign DNA is stably transformed into alfalfa.

3. The process of claim 1 wherein the cells are bombarded one to two times.

4. The process of claim 1 wherein the cotyledons are bombarded after imbibing water for about 24 hours to about 120 hours.

5. The process of claim 1 wherein the cotyledons are 10 to 15 days past pollination.

6. The process of claim 1 wherein the cotyledons are 10 days past pollination.

7. The process of claim 1 wherein the cells are cells of somatic embryos obtained from immature cotyledons.

8. A process of transforming foreign DNA into alfalfa plants comprising:
    attaching the foreign DNA to a carrier particle, accelerating the particle at immature cotyledon cells of alfalfa six to 25 days past pollination such that at least some of DNA is introduced in the interior of the cells, culturing the tissue on growth promoting medium, and cultivating the resulting growth into a whole mature alfalfa plant containing the introduced DNA.

* * * * *